United States Patent [19]

Guri

[11] Patent Number: 5,543,321
[45] Date of Patent: Aug. 6, 1996

[54] COLORED PLANT CULTURE MEDIA

[75] Inventor: Assaf Z. Guri, Cherry Hill, N.J.

[73] Assignee: Plant Cell Technology, Inc., Cherry Hill, N.J.

[21] Appl. No.: 329,598

[22] Filed: Oct. 26, 1994

[51] Int. Cl.$^6$ .................................................... C12N 5/02
[52] U.S. Cl. ............................. 435/240.4; 435/240.45; 435/240.54
[58] Field of Search ..................... 435/240.54, 240.45, 435/240.4

[56] References Cited

U.S. PATENT DOCUMENTS 3,923,729  12/1975  Clendinnig et al. .................. 435/240.4

OTHER PUBLICATIONS

Gollany et al., 1993, "Combined use of colorimetric and microelectrode methods for evaluating rhizosphere pH", Plant and Soil 154:151–159.

*Primary Examiner*—Chhaya D. Sayala
*Assistant Examiner*—L. Blaine Lankford
*Attorney, Agent, or Firm*—Pennie & Edmonds

[57] ABSTRACT

A sterilized plant culture medium comprising a dye in an amount which imparts a visible color to the culture medium and which permits seed germination is provided which is useful for attracting children, for observing and studying seed germination, root and shoot formation and whole plant development, and for color-coding plant cultures.

14 Claims, No Drawings

COLORED PLANT CULTURE MEDIA

FIELD OF THE INVENTION

The subject invention relates to colored plant culture media which are attractive to children, are useful to observe seed germination and plant growth, and can be used by students, researchers, plant breeders and plant nursery workers to color-code plant cultures.

BACKGROUND OF THE INVENTION

Seed germination and plant growth are fundamental biological processes of great scientific, educational and commercial interest. Parents and teachers often wish to present plant growth to children and students, respectively, in a way that is both informative and dynamic, allowing observations of growth and development over time. However, whereas the growth of the shoot, i.e., the aerial portions of the plant (leaves, flowers and fruits), can be directly observed, the germinating seed, as well as the developing root system, which is often as extensive as that of the shoot system, are usually buried in the soil. Weier, T. E., et al., *Botany: An Introduction to Plant Biology*, 6th Ed. John Wiley & Sons, Inc., pp. 158–76. Thus, seed germination and the developing root system are typically obscured.

Plants can be grown aseptically in tissue culture. The practice of growing plants and plant tissues on defined media in closed containers is well-developed. See, for example, Dixon, R. A. (ed), *Plant Cell Culture: A Practical Approach*, IRL Press, Oxford, Washington DC (1985). Plant tissue culture is typically carried out either in a liquid culture medium or on a solid culture medium solidified with a gelling agent, e.g., agar or gellan gum. In both liquid and solid culture, seed germination and the growth and development of shoots and roots can be directly observed. However, liquid culture typically requires constant agitation, for example, on a mechanical shaker, to maintain an adequate level of dissolved gases in the medium. Dixon, supra; Biondi and Thorpe, "Requirements for a Tissue Culture Facility" in: Plant Tissue Culture: Methods and Applications in Agriculture, Thorpe, T. A. (ed) Academic Press, (1981), pp. 1–20. Thus liquid culture is not well-suited for observation of plant growth in the home or in many educational, industrial or commercial situations.

The growth of plants on solid culture medium allows for the direct observation of seed germination and the growth and development of the whole plant, including the root system, since gelling agents, such as agar and gellan gum, are typically transparent. However, gelling agents are also colorless and, therefore, are not particularly attractive to children, nor do they provide an ability to color-code plant cultures.

Dyes have been incorporated into culture media for physiological studies. Gollany, H. T. and Schumacher, T. E., *Plant and Soil*, 154:151–59 (1993), describe the use of a pH-sensitive indicator dye, bromocresol purple, in agar medium to detect variations in pH along the length of the root.

Dyes, however, are often toxic or otherwise inhibitory to seed germination and plant growth, and so their general use in culture media is problematic. There are no reports of the incorporation of dyes into solid plant culture media in concentrations that impart a visible color to the culture medium and which permit seed germination. Furthermore, there are no reports of the use of such dyes to increase the attractiveness of aseptically cultured plants to children or for the color-coding of plant cultures for educational, research, industrial or commercial purposes.

SUMMARY OF THE INVENTION

It is an objective of the present invention to provide a plant culture medium in which to germinate plant seeds that allows seed germination and plant growth to be observed.

It is a further objective of the present invention to provide a plant culture medium that contains a dye in a concentration which imparts a visible color to the medium and which permits seed germination. Preferably, the dye concentration of the invention permits at least about 25% seed germination. More preferably, the dye concentration permits at least about 50% seed germination. And, most preferably, the dye concentration permits at least about 75% seed germination. Incorporation of the dye serves to increase the attractiveness of such plant cultures to children and provides students, researchers, plant breeders and plant nursery workers with the ability to color-code such cultures.

It is a further objective of the present invention to provide a method for germinating a plant seed comprising aseptically culturing the seed in said culture medium.

It is a further objective of the present invention to provide a kit for germinating a plant seed on said culture medium

DETAILED DESCRIPTION OF THE INVENTION

The present invention provides a culture medium in which to germinate seeds and grow plants that allows seed germination and plant growth to be observed. The present invention further provides a culture medium comprising a dye in a concentration which imparts a visible color to the medium and which permits seed germination, which color makes the culture medium more attractive to children, and which also allows students, researchers, plant breeders and plant nursery workers to color-code plant cultures.

Applicants have discovered that food color dyes, at empirically determined concentrations, will impart color to a solid plant culture medium and permit seed germination.

As used in the present application, germination is defined as the splitting of the seed coat and the emergence of a root tip therefrom.

As used in the present application, "culture medium" refers to a solid substrate or solution in which a plant seed will germinate or from which a plant will grow, and is intended to include water containing an appropriate mixture of mineral salts. The culture medium may also incorporate, in appropriate concentrations, plant hormones including, for example, auxins, cytokinins or gibberellins, vitamins, such as one or more B-vitamins, a carbon source including, for example, sucrose or glucose, and one or more undefined growth enhancers, such as coconut milk. The components of the mineral salts mixture may be selected and prepared in accordance with the requirements of the particular plant species being propagated. The appropriate composition of the mineral salts may either be empirically determined or selected from mineral salt compositions previously known in the plant tissue culture art and prepared accordingly. Alternatively, the mineral salts may be selected from any number of commercially available mixtures (e.g., from Sigma Chemical Co., St. Louis, Mo.). Mineral salt mixtures useful in the practice of the invention include, for example, Hoagland's basal salt mixture, Gamborg's B-5 basal salt mixture, Heller's basal salt mixture, Murashige and Skoog basal salt mixture, Nitsch and Nitsch basal salt mixture and White's basal salt mixture. In addition, various macronutrient, micronutrient and vitamin components known in the art may be variously combined to produce a culture medium appropriate to the plant species being propagated.

According to the present invention, a dye is added to a culture medium. The term "dye" is meant to include food color dyes certified by the United States Food and Drug Administration (FDA), as listed in 21 C.F.R. §74. According to the present invention, the dye is added to the culture medium in a concentration which will impart color to the medium and which will permit germination of a given plant seed of interest. Concentrations of dyes which are useful in the practice of the present invention range from about 5 µl to about 10 µl of commercially available food color dye (which is a 2.5% (w/v) stock solution of dye in distilled water) per 1 liter of culture medium.

The present invention further contemplates that food color dyes can be appropriately mixed. For example, FD&C Yellow No. 5 can be mixed with FD&C Blue No. 1 in appropriate proportions that, when added to a culture medium, will color the medium green. FD&C Yellow No. 5 can be mixed with FD&C Red No. 3 in appropriate proportions that, when added to a culture medium, will color the medium orange. FD&C Blue No. 1 can be mixed with FD&C Red No. 3 in appropriate proportions that, when added to a culture medium, will color the medium purple. The concentrations of such a dye mixture useful in the practice of the present invention will, as with unmixed dyes, range from about 5 µl to about 10 µl of the mixture of dyes (each dye being a 2.5% (w/v) stock solution of dye in distilled water) per 1 liter of culture medium.

After addition of the dye or dye mixture, a gelling agent, for example, PHYTAGEL™ gellan gum (Sigma Chemical Co.), in an appropriate concentration ranging, for example, from 0.2% to 0.3% (w/v) for gellan gum, is added to the culture medium and the pH is adjusted to, for example, 5.8, using 1N KOH. The culture medium is then autoclaved, for example, at 120° C. for 20 min, poured into sterilized culture containers, and allowed to cool and solidify. Heat-labile components of the culture medium, such as vitamins and sugars, may be filter-sterilized when appropriate according to known techniques and added to the autoclaved medium prior to its solidification.

Culture containers that may be used in practicing the invention are preferably transparent, and can be sterilized either by heat, chemical or radiation treatment. Culture containers may be composed of glass including, for example, borosilicate glass and soda glass, as well as plastics including, for example, transparent polystyrene and polypropylene. Culture containers include, but are not limited to, test-tubes and culture tubes, round-sided jars, bottles and flasks, and square-sided jars, bottles and flasks, which may be arranged individually or in multi-container racks or trays, and which may be configured so as to allow for stacking.

The present invention contemplates the addition of a dye or dye mixture to culture media to allow students, researchers, plant breeders and plant nursery workers to color-code plant cultures, for example, where plant seeds of particular species or varieties are grown on media of particular colors, or where media containing different culture components such as, for example, differing types or concentrations of mineral salts, hormones or carbon sources, are differently colored. Such differently colored media can be used to effectively facilitate the sorting, maintenance and monitoring of large numbers of culture containers.

Dyes and dye mixtures can also be used to color media to correspond to particular calendar events. For example, seed germination kits sold at Christmas can contain culture medium dyed red or green, or both by, for example, layering red culture medium over previously solidified green culture medium, with an impermeable layer, for example, plastic food wrap, placed between layers to prevent diffusion of colors. Kits sold at Valentine's Day can contain culture medium dyed pink, those sold at St. Patrick's Day can contain culture medium dyed green, and those sold at Halloween can be dyed orange.

Seeds of any plant species can be germinated in the culture medium of the invention. Such seeds can come from any appropriate species of dicotyledonous, monocotyledonous or gymnospermous plant, including any woody plant species that grows as a tree or shrub, any herbaceous species, any species that produces edible fruits, seeds or vegetables, and any species that produces colorful or aromatic flowers. In addition, for purposes of this invention, the term "plant seed" encompasses the spores of ferns and other lower vascular plants, as well as the spores of non-vascular plants such as mosses, liverworts and hornworts.

Prior to placing the seed into the culture medium, it is preferred that the seed be surface-sterilized to remove fungal or bacterial spores. Surface-sterilization can be accomplished using any generally available sterilizing agent, but household bleach diluted in water is preferred. Seeds may be effectively surface-sterilized by, for example, immersing them in a dilute solution of household bleach in water at a concentration, for example, of about 5% (v/v) to about 20% bleach, with or without a surfactant, for a time sufficient to surface-sterilize the seed, for example, from about 10 min to about 120 min, and then rinsing the seeds 3x with sterilized water.

The surface-sterilized seed may either be immediately and aseptically inserted into or on the solidified culture medium and the culture container sealed, or the surface-sterilized seed may be placed in a separate "seed container" to maintain its surface-sterility. This seed container would then accompany the culture container containing the culture medium, with instructions to the end-user on how to transfer the seed to the medium in the culture container without compromising the sterility of the components. The end-user would then have the opportunity to initiate the culture and to observe germination.

The present invention further contemplates that more than one seed may be provided with, or in, a culture container to compensate for species where less than 100% seed germination is anticipated.

The present invention further contemplates that the culture container can be opened and the plant removed at any stage of growth for transfer of the plant to another substrate such as, for example, soil or vermiculite, for continued growth.

Having now generally described the invention, the same will be more readily understood through reference to the following example which is provided by way of illustration, and is not intended to be limiting of the present invention.

EXAMPLE

EFFECT OF FD&C YELLOW NO. 5, FD&C BLUE NO. I AND FD&C RED NO. 3 FOOD COLOR DYES ON THE GERMINATION OF PLANT SEEDS

The effect of various concentrations of food color dyes on the germination of a wide variety of seeds was tested using commercially available (Durkee, San Francisco, Calif.) synthetic dyes certified by the United States Food and Drug Administration.

Culture media containing food color dye were prepared as follows. Five to 30 μl of dye (from a commercially available 2.5% (w/v) stock solution of dye in distilled water), for example, FD&C Yellow No. 5 food color dye (which is principally the trisodium salt of 4,5-dihydro-5-oxo-1-(4-sulfophenyl)-sulfophenyl)-4-[4-sulfophenyl-azo]-1H-pyrazole-3-carboxylic acid; CAS Reg. No. 1934-21-0) (see 21 C.F.R. §74.705), were added to 1 liter of culture medium containing 1.6 gm of Hoagland's No. 2 basal salt mixture (Sigma Chemical Co., Sigma Catalog No. H2395) and 2% (w/v) sucrose. PHYTAGEL™ gellan gum (Sigma Chemical Co.) was added to the solution at a concentration of 0.2 to 0.3% (w/v) and the solution was adjusted to pH 5.8 using a solution of 1N KOH. The solution was then autoclaved at 120° C. for 20 min, allowed to partially cool, poured into sterilized plastic or glass culture vessels, and allowed to cool to room temperature to solidify.

Seeds of a variety of plants were tested for their ability to germinate on culture media prepared as above. Germination percentages were generated by testing 1,000 seeds (100 seeds per experiment, 10 repetitions) of each plant species at each dye concentration in the dark at 25°–28° C. Results are presented in Table 1. The percentage of seed germination declined dramatically with an increase in the concentration of FD&C Yellow No. 5 in the culture medium. At 20 μl of FD&C Yellow No. 5 per 1 liter culture medium, most seeds of most plant species tested did not germinate. Only seeds of apple, papaya, orange and lemon germinated at that concentration, and only at greatly reduced percentages. A dye concentration of 5 μl of FD&C Yellow No. 5 per liter of culture medium permitted seed germination for all plant species tested. Although the germination percentage for tobacco was greatly reduced, some germination was still observed (1–24%).

Seed germination was also tested as above on culture medium prepared as above, but containing FD&C Blue No. 1 food color dye, which is principally the disodium salt of ethyl [4-[p-[ethyl(m-sulfobenzyl)amino]-α-(o-sulfophenyl)benzylidene]-2,5-cyclohexadien-1-ylidene](m-sulfobenzyl) ammonium hydroxide inner salt (see 21 C.F.R. §74.101), rather than FD&C Yellow No. 5 food color dye. The results, which are presented in Table 2, were the same as those obtained on culture medium containing FD&C Yellow No. 5 food color dye except for the higher germination of pepper at 10 μl.

Seed germination was also tested as above on culture medium prepared as above, but containing FD&C Red No. 3 food color dye, which is principally the monohydrate of 9(o-carboxyphenyl)-6-hydroxy-2,4,5,7-tetraiodo-3H-xanthen-3-one, disodium salt (see 21 C.F.R. §74.303), rather than FD&C Yellow No. 5 food color dye. The results, which are presented in Table 3, were the same as those obtained on culture medium containing FD&C Yellow No. 5 food color dye.

The raw data from the testing of each of the three dyes, FD&C Yellow No. 5, FD&C Blue No. 1 and FD&C Red No. 3, as described above, are provided in Table 4.

TABLE 1

EFFECT OF INCREASING CONCENTRATIONS OF FD&C YELLOW NO 5 FOOD COLOR DYE ON PLANT SEED GERMINATION*

| Seed types | Food color dye (FD&C Yellow No. 5) concentration in μl of dye per 1 liter of culture medium | | | | | | |
|---|---|---|---|---|---|---|---|
| | 0 | 5 | 10 | 15 | 20 | 25 | 30 |
| pepper | ++++ | ++++ | +++ | + | − | − | − |
| tomato | ++++ | ++++ | ++ | − | − | − | − |
| eggplant | ++++ | ++++ | ++ | − | − | − | − |
| apple | ++++ | ++++ | +++ | ++ | + | − | − |
| pear | ++++ | ++++ | +++ | + | − | − | − |
| papaya | ++++ | ++++ | ++++ | +++ | + | − | − |
| beans (navy) | ++++ | ++++ | ++ | + | − | − | − |
| peas | ++++ | ++++ | ++ | − | − | − | − |
| watermelon | ++++ | ++++ | +++ | ++ | − | − | − |
| cucumber | ++++ | ++++ | ++ | + | − | − | − |
| pomegranate | ++++ | ++++ | + | − | − | − | − |
| orange | ++++ | ++++ | ++++ | ++ | + | − | − |
| lemon | ++++ | ++++ | ++++ | ++ | + | − | − |
| coffee | ++++ | ++++ | +++ | + | − | − | − |
| Douglas fir | ++++ | ++ | + | − | − | − | − |
| tobacco | ++++ | + | − | − | − | − | − |
| kiwi | ++++ | ++ | + | − | − | − | − |

*The data were generated by testing 1,000 seeds (100 seeds × 10 repetitions) of each plant species at each concentration. Germination: ++++ = 75–100%, +++ = 50–74%, ++ = 25–49%, + = 1–24%, − = no germination.

TABLE 2

EFFECT OF INCREASING CONCENTRATIONS OF FD&C BLUE NO. 1 FOOD COLOR DYE ON PLANT SEED GERMINATION*

| Seed types | Food color dye (FD&C Blue No. 1) concentration in μl of dye per 1 liter of culture medium | | | | | | |
|---|---|---|---|---|---|---|---|
| | 0 | 5 | 10 | 15 | 20 | 25 | 30 |
| pepper | ++++ | ++++ | ++++ | + | − | − | − |
| tomato | ++++ | ++++ | ++ | − | − | − | − |
| eggplant | ++++ | ++++ | ++ | − | − | − | − |
| apple | ++++ | ++++ | +++ | ++ | + | − | − |
| pear | ++++ | ++++ | +++ | + | − | − | − |
| papaya | ++++ | ++++ | ++++ | +++ | + | − | − |
| beans (navy) | ++++ | ++++ | ++ | + | − | − | − |
| peas | ++++ | ++++ | ++ | − | − | − | − |
| watermelon | ++++ | ++++ | +++ | ++ | − | − | − |
| cucumber | ++++ | ++++ | ++ | + | − | − | − |
| pomegranate | ++++ | ++++ | + | − | − | − | − |
| orange | ++++ | ++++ | ++++ | ++ | + | − | − |
| lemon | ++++ | ++++ | ++++ | ++ | + | − | − |
| coffee | ++++ | ++++ | +++ | + | − | − | − |
| Douglas fir | ++++ | ++ | + | − | − | − | − |
| tobacco | ++++ | + | − | − | − | − | − |
| kiwi | ++++ | ++ | + | − | − | − | − |

*The data were generated by testing 1,000 seeds (100 seeds × 10 repetitions) of each plant species at each concentration. Germination: ++++ = 75–100%, +++ = 50–74%, ++ = 25–49%, + = 1–24%, − = no germination.

TABLE 3

EFFECT OF INCREASING CONCENTRATIONS OF FD&C RED NO. 3 FOOD COLOR DYE ON PLANT SEED GERMINATION*

Food color dye (FD&C Red No. 3) concentration in μl if dye per 1 liter of culture medium

| Seed types | 0 | 5 | 10 | 15 | 20 | 25 | 30 |
|---|---|---|---|---|---|---|---|
| pepper | ++++ | ++++ | +++ | + | − | − | − |
| tomato | ++++ | ++++ | ++ | − | − | − | − |
| eggplant | ++++ | ++++ | ++ | − | − | − | − |
| apple | ++++ | ++++ | +++ | ++ | + | − | − |
| pear | ++++ | ++++ | +++ | + | − | − | − |
| papaya | ++++ | ++++ | ++++ | +++ | + | − | − |
| beans (navy) | ++++ | ++++ | ++ | + | − | − | − |
| peas | ++++ | ++++ | ++ | − | − | − | − |
| watermelon | ++++ | ++++ | +++ | ++ | − | − | − |
| cucumber | ++++ | ++++ | ++ | + | − | − | − |
| pomegranate | ++++ | ++++ | + | − | − | − | − |
| orange | ++++ | ++++ | ++++ | ++ | + | − | − |
| lemon | ++++ | ++++ | ++++ | ++ | + | − | − |
| coffee | ++++ | ++++ | +++ | + | − | − | − |
| Douglas fir | ++++ | ++ | + | − | − | − | − |
| tobacco | ++++ | + | − | − | − | − | − |
| kiwi | ++++ | ++ | + | − | − | − | − |

*The data were generated by testing 1,000 seeds (100 seeds × 10 repetitions) of each plant species at each concentration. Germination: ++++ = 75–100%, +++ = 50–74%, ++ = 25–49%, + = 1–24%, − = no germination.

TABLE 4

EFFECT OF INCREASING CONCENTRATIONS OF SELECTED FOOD COLOR DYES ON PLANT SEED GERMINATION*

Food color dye concentration in μl of dye per liter of culture medium

| Seed types | 0 | 5 y | 5 b | 5 r | 10 y | 10 b | 10 r | 15 y | 15 b | 15 r | 20 y | 20 b | 20 r | 25 y | 25 b | 25 r | 30 y | 30 b | 30 r |
|---|---|---|---|---|---|---|---|---|---|---|---|---|---|---|---|---|---|---|---|
| pepper | 97 | 89 | 86 | 88 | 72 | 75 | 74 | 16 | 14 | 15 | 0 | 0 | 0 | 0 | 0 | 0 | 0 | 0 | 0 |
| tomato | 98 | 79 | 80 | 81 | 43 | 41 | 39 | 0 | 0 | 0 | 0 | 0 | 0 | 0 | 0 | 0 | 0 | 0 | 0 |
| eggplant | 91 | 83 | 83 | 82 | 44 | 45 | 43 | 0 | 0 | 0 | 0 | 0 | 0 | 0 | 0 | 0 | 0 | 0 | 0 |
| apple | 93 | 89 | 91 | 92 | 65 | 66 | 66 | 29 | 27 | 30 | 13 | 11 | 14 | 0 | 0 | 0 | 0 | 0 | 0 |
| pear | 96 | 88 | 92 | 90 | 69 | 64 | 67 | 12 | 12 | 14 | 0 | 0 | 0 | 0 | 0 | 0 | 0 | 0 | 0 |
| papaya | 98 | 89 | 92 | 94 | 80 | 78 | 76 | 72 | 74 | 71 | 18 | 16 | 20 | 0 | 0 | 0 | 0 | 0 | 0 |
| beans (navy) | 99 | 90 | 87 | 90 | 37 | 36 | 32 | 16 | 18 | 14 | 0 | 0 | 0 | 0 | 0 | 0 | 0 | 0 | 0 |
| peas | 93 | 82 | 86 | 88 | 37 | 32 | 31 | 0 | 0 | 0 | 0 | 0 | 0 | 0 | 0 | 0 | | | |
| watermelon | 89 | 81 | 81 | 81 | 66 | 69 | 72 | 30 | 27 | 26 | 0 | 0 | 0 | 0 | 0 | 0 | 0 | 0 | 0 |
| cucumber | 96 | 77 | 81 | 78 | 47 | 46 | 49 | 12 | 9 | 7 | 0 | 0 | 0 | 0 | 0 | 0 | 0 | 0 | 0 |
| pomegranate | 96 | 83 | 80 | 79 | 9 | 10 | 13 | 0 | 0 | 0 | 0 | 0 | 0 | 0 | 0 | 0 | 0 | 0 | 0 |
| Orange | 99 | 92 | 96 | 96 | 86 | 84 | 87 | 33 | 36 | 32 | 8 | 12 | 9 | 0 | 0 | 0 | 0 | 0 | 0 |
| lemon | 93 | 90 | 91 | 91 | 83 | 84 | 80 | 42 | 39 | 43 | 20 | 22 | 18 | 0 | 0 | 0 | 0 | 0 | 0 |
| coffee | 89 | 82 | 83 | 79 | 61 | 63 | 65 | 11 | 8 | 10 | 0 | 0 | 0 | 0 | 0 | 0 | 0 | 0 | 0 |
| Douglas fir | 84 | 40 | 35 | 37 | 11 | 10 | 8 | 0 | 0 | 0 | 0 | 0 | 0 | 0 | 0 | 0 | 0 | 0 | 0 |
| tobacco | 96 | 13 | 16 | 14 | 0 | 0 | 0 | 0 | 0 | 0 | 0 | 0 | 0 | 0 | 0 | 0 | 0 | 0 | 0 |
| kiwi | 77 | 41 | 41 | 39 | 8 | 7 | 11 | 0 | 0 | 0 | 0 | 0 | 0 | 0 | 0 | 0 | 0 | 0 | 0 |

*Numbers represent percent germination for each treatment. The data were generated by testing 1,000 seeds (100 seeds × 10 repetitions) of each plant species at each concentration. y = FD&C Yellow No. 5, b = FD&C Blue No. 1, r = FD&C Red No. 3.

Having now fully described this invention, it will be appreciated by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is intended to cover any variations, uses, or adaptations of the invention following, in general, the principles of the invention and including such departures from the present disclosure as come within known or customary practice within the art to which the invention pertains and as may be applied to the essential features hereinbefore set forth as follows in the scope of the appended claims.

All publications cited above are herein incorporated by reference.

What is claimed is:

1. A sterilized culture medium for the germination of a plant seed, comprising a dye in a concentration which imparts a visible color to the culture medium and which permits seed germination wherein the dye is selected from the group consisting of FD&C Yellow No. 5, FD&C Blue No. 1, FD&C Red No. 3, and mixtures thereof and wherein concentration of the dye is about 5 μl to about 10 μl of a 2.5% (w/v) dye stock solution per 1 liter of medium.

2. The culture medium of claim 1, in which the concentration of dye is 5 μl of a 2.5% (w/v) dye stock solution per 1 liter of culture medium.

3. The culture medium of claim 1, further comprising a gelling agent.

4. The culture medium of claim 1 contained in a sterilized culture container.

5. The culture medium of claim 4, further comprising a plant seed.

6. The culture medium of claim 5, in which the plant seed is selected from a species that produces edible vegetables.

7. The culture medium of claim 5, in which the plant seed is selected from a species that produces edible fruits or edible seeds.

8. The culture medium of claim 5, in which the plant seed is selected from a species that produces trees or shrubs.

9. The culture medium of claim 5, in which the plant seed is selected from an herbaceous species.

10. The culture medium of claim 5, in which the plant seed is selected from a species that produces flowers.

11. The culture medium of claim 5, in which the plant seed is from Douglas fir.

12. The culture medium of claim 7, in which the plant seed is selected from the group consisting of pepper, tomato, eggplant, apple, pear, papaya, bean, pea, watermelon, cucumber, pomegranate, orange, lemon, coffee and kiwi.

13. A method for germinating a plant seed comprising aseptically culturing the seed in a culture container comprising a sterilized culture medium comprising a dye in a concentration which imparts a visible color to the culture medium and which permits seed germination wherein the dye is selected from the group consisting of FD&C Yellow No. 5, FD&C Blue No. 1, FD&C Red No. 3, and mixtures thereof and wherein concentration of the dye is about 5 µl to about 10 µl of a 2.5% (w/v) dye stock solution per 1 liter of medium.

14. The method of claim 13, in which the concentration of dye is 5 µl of a 2.5% (w/v) dye stock solution per 1 liter of culture medium.

* * * * *